(12) United States Patent
Angeley (10) Patent No.: US 7,027,163 B2
(45) Date of Patent: Apr. 11, 2006

(54) GRATING SENSOR

(75) Inventor: David Angeley, Charlottesville, VA (US)

(73) Assignee: General Dynamics Advanced Information Systems, Inc., Arlington, VA (US)

(*) Notice: Subject to any disclaimer, the term of this patent is extended or adjusted under 35 U.S.C. 154(b) by 162 days.

(21) Appl. No.: 10/350,508

(22) Filed: Jan. 24, 2003

(65) Prior Publication Data

US 2004/0145752 A1    Jul. 29, 2004

(51) Int. Cl.
*G01B 9/02* (2006.01)
*G01N 21/00* (2006.01)
*G01N 21/03* (2006.01)

(52) U.S. Cl. .................. 356/521; 356/244; 436/165

(58) Field of Classification Search ............... 356/521, 356/244, 246, 436, 440; 422/82.05–82.11; 436/114–172
See application file for complete search history.

(56) References Cited

U.S. PATENT DOCUMENTS

| | | | |
|---|---|---|---|
| 4,487,839 A | 12/1984 | Kamentsky | |
| 4,517,456 A | 5/1985 | Halsall et al. | |
| 4,876,208 A | 10/1989 | Gustafson et al. | |
| RE33,581 E | 4/1991 | Nicoli et al. | |
| 5,071,248 A | 12/1991 | Tiefenthaler et al. | |
| 5,081,012 A | 1/1992 | Flanagan et al. | |
| 5,082,629 A | 1/1992 | Burgess, Jr. et al. | |
| 5,196,350 A | 3/1993 | Backman et al. | |
| 5,413,939 A | 5/1995 | Gustafson et al. | |
| 5,442,169 A | 8/1995 | Kunz | |
| 5,559,601 A | 9/1996 | Gallatin et al. | |
| 5,577,137 A | 11/1996 | Groger et al. | |
| 5,578,833 A | 11/1996 | Ohmi et al. | |
| 5,679,579 A | 10/1997 | Gustfason | |
| 5,846,843 A | 12/1998 | Simon | |
| 5,922,550 A | 7/1999 | Everhart et al. | |
| 5,959,292 A | 9/1999 | Duveneck et al. | |
| 5,999,319 A | 12/1999 | Castracane | |
| 6,060,256 A * | 5/2000 | Everhart et al. ............ 436/164 |
| 6,061,166 A | 5/2000 | Furlani et al. | |
| 6,180,266 B1 | 1/2001 | Everhart et al. | |
| 6,180,288 B1 | 1/2001 | Everhart et al. | |
| 6,221,579 B1 | 4/2001 | Everhart et al. | |
| 6,312,961 B1 | 11/2001 | Vorin et al. | |
| 6,326,144 B1 | 12/2001 | Bawendi et al. | |
| 6,333,507 B1 | 12/2001 | Lai et al. | |

(Continued)

*Primary Examiner*—Gregory J. Toatley, Jr.
*Assistant Examiner*—Patrick J. Connolly
(74) *Attorney, Agent, or Firm*—Michael J. Bell; Howrey LLP (57) ABSTRACT

A fast, accurate and reliable sensor applicable to chemical and biological analytes resides in an optical grating-based sensor, sensing system, and method of use. The sensor, configured for use with an illumination source and a signal detector in the system embodiment, includes first and second periodic diffraction gratings superimposed and shifted laterally relative to each other by a distance of less than one period, such that the illumination from the source is affected by both gratings before reaching the detector. An analyte recognition material disposed on a surface of the second diffraction grating. In operation, the output of the detector is first used to establish a baseline optical phase signal. The analyte recognition material is exposed to a sample, and the output of the detector is used to to determine a second optical phase signal. The baseline optical phase signal is compared to the second optical phase signal to detect the presence of the analyte, if any, in the sample. The analyte recognition material may be an antibody, nucleic acid, lectin or other substance. The sample may obtained from a mammal, including a human, plant, or the environment.

25 Claims, 8 Drawing Sheets

U.S. PATENT DOCUMENTS

| | | |
|---|---|---|
| 6,384,959 B1 | 5/2002 | Furlani et al. |
| 6,429,022 B1 * | 8/2002 | Kunz et al. ............... 436/164 |
| 6,433,911 B1 | 8/2002 | Chen et al. |
| 6,445,433 B1 | 9/2002 | Levola |
| 6,455,004 B1 | 9/2002 | Tiefenthaler |
| 6,483,096 B1 | 11/2002 | Kunz et al. |
| 6,485,690 B1 | 11/2002 | Pfost et al. |
| 6,518,168 B1 | 2/2003 | Clem et al. |
| 6,549,687 B1 | 4/2003 | Kochergin et al. |
| 6,579,673 B1 | 6/2003 | McGrath et al. |
| 6,590,695 B1 | 7/2003 | Kurtz et al. |
| 6,600,149 B1 | 7/2003 | Schulz et al. |
| 6,643,065 B1 | 11/2003 | Silberman |
| 2001/0003028 A1 | 6/2001 | Ebihara |
| 2001/0004526 A1 | 6/2001 | Everhart et al. |
| 2001/0055754 A1 | 12/2001 | McGrath et al. |
| 2002/0043651 A1 | 4/2002 | Darrow et al. |
| 2002/0054424 A1 | 5/2002 | Miles |
| 2002/0074513 A1 | 6/2002 | Abel et al. |
| 2002/0149834 A1 | 10/2002 | Mei et al. |
| 2002/0167245 A1 | 11/2002 | Hung et al. |
| 2002/0168295 A1 | 11/2002 | Cunningham et al. |
| 2003/0007896 A1 | 1/2003 | Tiefenthaler |
| 2003/0012692 A1 | 1/2003 | Lemee et al. |
| 2003/0027328 A1 | 2/2003 | Cunningham et al. |
| 2003/0048437 A1 | 3/2003 | Kalal et al. |
| 2003/0081875 A1 | 5/2003 | Kochetgin et al. |
| 2003/0107740 A1 | 6/2003 | Kaylor et al. |
| 2003/0118480 A1 | 6/2003 | Kaylor et al. |
| 2003/0133640 A1 | 7/2003 | Tiefenthaler |
| 2003/0168587 A1 | 9/2003 | Tiefenthaler |
| 2003/0201385 A1 | 10/2003 | Schulz et al. |
| 2003/0234341 A1 | 12/2003 | Osborn |
| 2004/0002110 A1 | 1/2004 | Boga et al. |
| 2005/0068543 A1 * | 3/2005 | Angeley ..................... 356/521 |

* cited by examiner

GRATING SENSOR

FIELD OF THE INVENTION

This invention relates to sensor devices for detecting chemical and biological agents. In particular, the invention relates to chemical and biological agent sensor devices that detect phase changes in light incident on two diffraction gratings.

BACKGROUND OF THE INVENTION

Biological weapons, infectious diseases, and environmental pathogens threaten both military and civilian personnel. Current technology lacks the capability to accurately detect the presence of trace amounts of chemical and biological warfare agents quickly and reliably.

Current technologies include those involving detection of analytes labeled with a fluorescent, photo-luminescent, radioactive or enzymatic marker. This requirement includes additional steps and expense to the detection process, a significant disadvantage when prompt detection is necessary.

Another broad category of currently used sensors includes those that employ optical waveguides. Waveguide sensors typically have the disadvantages of high sensitivity to changes in the ambient conditions such as temperature, resulting in undesirable signal to noise ratios.

Other known sensors monitor changes in the intensity of several diffraction orders to detect the occurrence of a biological binding event. However, intensity (irradiance) measurements are not sensitive enough for many applications and are sensitive to noise, resulting in difficulty in relating and quantifying the changes in the detected diffraction irradiance signal to an input stimulus.

SUMMARY OF THE INVENTION

This invention improves upon the existing art by proving a fast, accurate and reliable sensor applicable to chemical and biological analytes. The invention covers an optical grating-based sensor, sensing system, and method of use. The sensor, configured for use with an illumination source and a signal detector in the system embodiment, includes first and second periodic diffraction gratings superimposed and shifted laterally relative to each other by a distance of less than one period, such that the illumination from the source is affected by both gratings before reaching the detector. An analyte recognition material disposed on a surface of the second diffraction grating.

Given this arrangement with the illumination source activated, the output of the detector is first used to establish a baseline optical phase signal. The analyte recognition material is exposed to a sample, and the output of the detector is used to determine a second optical phase signal. The baseline optical phase signal is compared to the second optical phase signal to detect the presence of the analyte, if any, in the sample.

The analyte recognition material may be an antibody, nucleic acid, lectin or other substance. The sample may be obtained from a mammal, including a human, plant, or the environment. A positioning system may be provided for moving one or both of the first and second gratings, and the system may further comprise a spatial filter disposed relative to the second grating such that selected orders of diffracted light are prevented from reaching the detector.

DETAILED DESCRIPTION OF THE INVENTION

A grating sensor according to the present invention is a photonic device that includes an optical grating structure having at least two individual gratings. The two gratings, each having a periodic structure, are positioned parallel to each other, such that the periodic structure are superimposed and shifted laterally relative to each other. This lateral shift is less than one period and is preferably a shift of one quarter period. Further, at least one of the gratings includes an analyte recognition material operable to interact specifically with an analyte of interest. A change in the depth of modulation in one of the gratings caused by specific interaction of an analyte with an analyte recognition material results in a change in optical phase. The phase change is sensed by a detector and output as signal. The grating sensor may further include a translation device adapted to move one or more of the gratings in order to modulate the signal.

Figure 1:
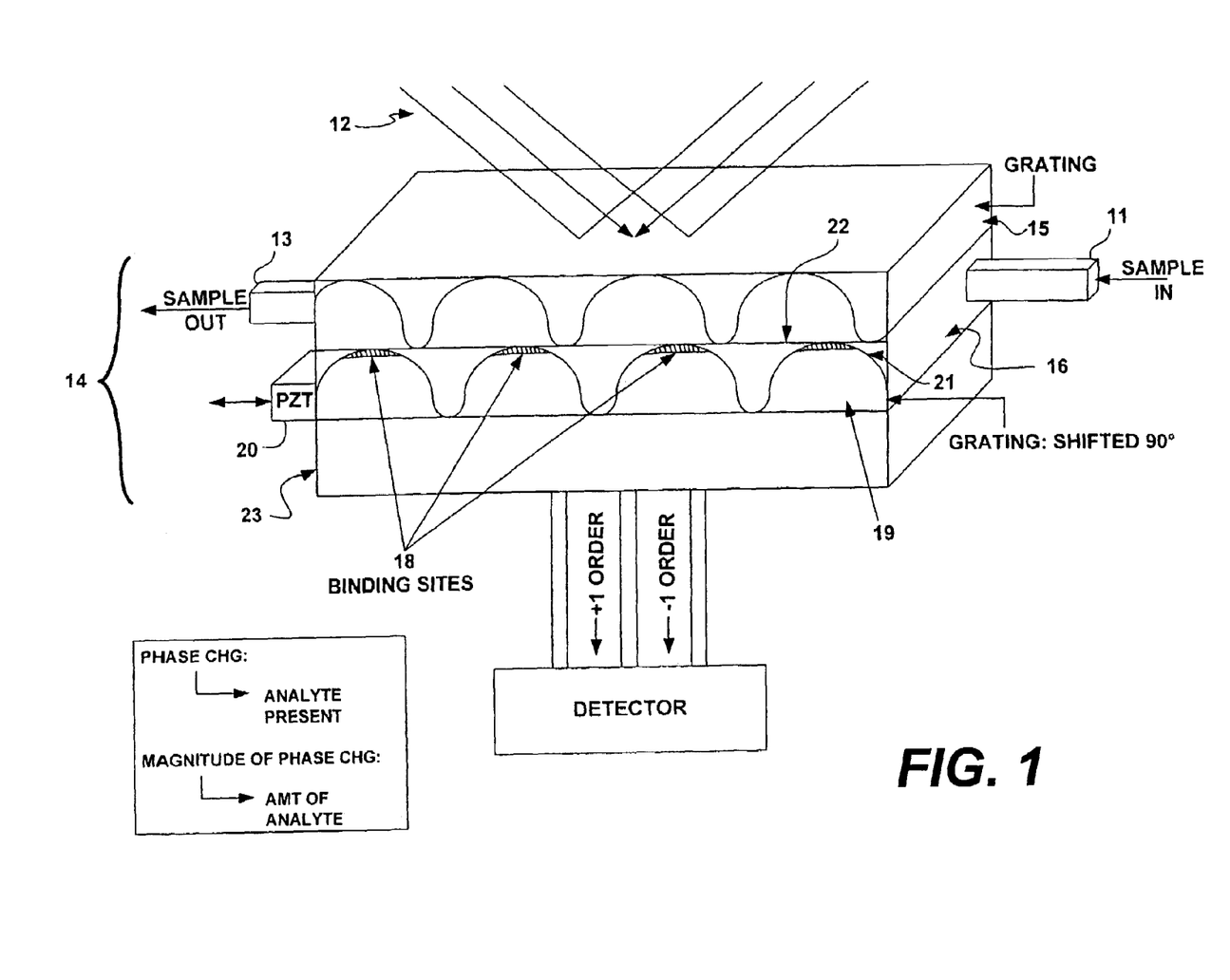
FIG. 1 is a drawing illustrating an embodiment of a grating sensor according to the present invention.

FIG. 1 illustrates the grating sensor generally at 10. Incident light 12 is scattered or diffracted into specific orders by a grating structure 14 including two gratings 15, 16. The properties of this scattered light are determined by various features that compose the grating structure 14. A physical change in the grating structure 14, caused by interaction of an analyte 18 with an analyte recognition material 19 on the grating structure 14, causes a change in light which is detected as a change in optical phase. Changes in the optical phase of the scattered light transmitted through the grating structure are detected by a detector 17 and measured. Also shown is a positioning system 20 which modulates the output signal by moving one or more of the gratings.

Figure 2:
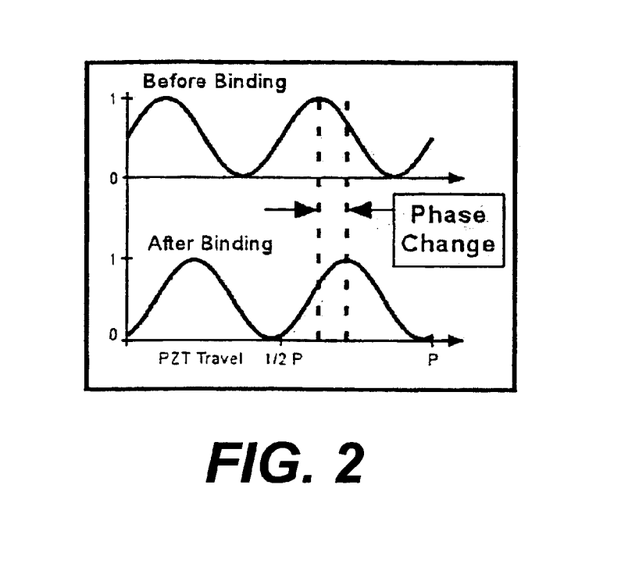
FIG. 2 is a drawing illustrating output data of a grating sensor according to the present invention.

FIG. 2 illustrates an exemplary output signal showing a change in optical phase occurring following binding of an analyte to an analyte recognition material.

Gratings

Gratings suitable for use in an inventive sensor and methods of their generation are known in the art. A grating is selected for a particular sensor application according to characteristics and properties required, which will be recognized by one of skill in the art. Characteristics and modifiable properties of individual gratings and their uses are set forth in references such as Hutley M. et al.; Diffraction Gratings; Academic Press; 1997 and E. Popov, et al., Diffraction Gratings and Applications; Marcel Dekker, Inc.; 1997. Modifiable grating parameters illustratively include period, index of refraction and modulation depth. The period of the grating determines the scatter angle of the diffracted orders; the peak-to-valley depth of the phase (i.e. refractive index) profile determines the amount of light that is diffracted into each order; and the lateral position of the grating determines the phase of the wavefront in each of the diffracted orders relative to the zero order. Further modifiable grating parameters include material composition of the grating, grating surface chemistry and type of analyte recognition material used, as described below.

An illustrative grating suitable for use in a sensor according to the present invention is described in Example 1 below.

Grating Composition

A grating suitable for use in an inventive sensor includes a substrate material. The substrate material is a solid or firm gel illustratively including glass, silicon, metals such as aluminum, copper, gold, platinum titanium, alloys thereof, graphite, mica, and various polymers, such as polystyrene; polycarbonate; polymethylmethacrylate; polyvinylethylene; polyethyleneimine; polyoxymethylene; polyvinylphenol; polylactides; polymethacrylimide; polyalkenesulfone; polyhydroxyethylmethacrylate; polyvinylidenedifluoride; polydimethylsiloxane; polytetrafluorethylene; polyacrylamide; polyimide and block-copolymers. Choice of grating material depends on a number of factors such as the analyte sought to be detected, the analyte recognition material to be used and the surface chemistry suitable for immobilizing the analyte recognition material on the grating. Bowtell et al., DNA Microarrays: A Molecular Cloning Manual, Cold Spring Harbor Laboratory; 2002.

Grating Surface Chemistry

The substrate material of a grating used in an inventive sensor may have a modified surface for immobilizing an analyte recognition material by chemical bonding or adsorption. Surface modification, such as by chemical treatment of a surface to provide binding sites for an analyte recognition material depends on the particular analyte recognition material to be attached to the substrate and the composition of substrate. Modification of grating surface chemistry in order to attach an analyte recognition material is well known in the art and includes such illustrative methods as modification of silicon or silicon oxide surfaces with organo-functionalized silanes. such as alkoxy- and chloro-silanes. Further suitable silanes are listed in Silicon Compounds: Register & Review, from United Chemical Technologies, 5th Ed., 1991. In addition, many other surface chemistries and methods of modifying a grating substrate for binding an analyte recognition material are known, such as those commonly used to fabricate microarrays of proteins, nucleic acids and other materials. See, for example, M. Schena, et al., "Quantitative Monitoring of Gene Expression Patterns with a Complementary DNA Microarray", Science, 270: 467–470, 1995; Hermanson et al., in Immobilized Affinity Ligand Techniques, Academic Press, Inc., 1992 and U.S. Pat. Nos. 6,479,301, 6,475,809, 6,444,318 and 6,410,229.

Advantageously, attachment of an analyte recognition material may be reversible such that the sensing surface of the grating is reusable.

Analyte Recognition Materials

An analyte recognition material is included on at least one of the gratings used in a sensor of the invention. As used herein, the term "analyte recognition material" is intended to mean a molecule that specifically binds to an entity to be detected, an analyte.

Analytes detected by a grating sensor according to the invention illustratively include an antibody, an antigen, a hapten, a receptor, a receptor ligand such as an agonist or antagonist, a lectin, a protein, a peptide, a polysaccharide, a toxin, a virus, a bacterium, a cell, a cell component such as an organelle, a particle such as a liposome or niosome, a nucleic acid, a drug and a prion. An analyte may be a fragment or metabolite of the substances listed above capable of specific interaction with an analyte recognition material. Nucleic acids illustratively include DNA, RNA, oligomers and aptamers. An analyte may also be a gas, illustratively including NO, $O_2$ and $CO_2$.

Exemplary analyte recognition materials immobilized on a grating of the inventive sensor include an antigen, antibody, hapten, carbohydrate, lectin, receptor, ligand, binding protein, toxin, substrate, enzyme and nucleic acid.

Specific interactions between an analyte and an analyte recognition material are well known in the art, as are reaction conditions under which specific interactions occur. Interactions an analyte and an analyte recognition material illustratively include those of the following types: antigen-antibody, carbohydrate-lectin, receptor-ligand, binding protein-toxin, substrate-enzyme, effector-enzyme, inhibitor-enzyme, nucleic acid pairing, binding protein-vitamin, binding protein-nucleic acid, reactive dye-protein, and reactive dye-nucleic acid. Reactions conditions include variables such as temperature, salt concentrations, pH and reaction time are known to affect binding and one of skill in the art will recognize the appropriate binding conditions for a particular analyte/analyte recognition material pair. Specific conditions are set forth in common references such as, for example, Bowtell et al., DNA Microarrays: A Molecular Cloning Manual, Cold Spring Harbor Laboratory; 2002; Sambrook et al., Molecular Cloning: A Laboratory Manual, Cold Spring Harbor Laboratory; 3rd edition, 2001; and Harlow et al., Using Antibodies: A Laboratory Manual: Portable Protocol No. I, Cold Spring Harbor Laboratory; 1998.

Deposition of Analyte Recognition Material on Grating Surface

Creating structured arrays of analyte recognition materials requires immobilization of those materials at discrete locations on the surface of a grating used in an inventive sensor. Deposition and patterning of an analyte recognition material on a grating is known in the prior art. Exemplary techniques used include photoresist technology, self-assembled monolayer deposition and photochemical techniques. Deposition and patterning are particularly important as a variable contributing to the refractive index of a particular grating. Adjustment of the refractive index of a grating may be one method of modulating the sensitivity of the grating sensor.

An exemplary method of analyte recognition material deposition and patterning is micro-contact printing, which is a type of soft lithography that transfers molecules onto substrates at specific locations with the use of a polymeric stamp that has been cast from a desired pattern or mold. This procedure is an established microfabrication technique for patterning chemicals, proteins, DNA, lipid membranes, and cells. A polymer stamp, typically a material such as poly dimethyl siloxane, has the analyte recognition material to be patterned adsorbed to it, rinsed and dried, and then placed into contact with a solid substrate. After some determined time, seconds to minutes, the stamp is removed and the substrate surface is left with a coating of the transferred analyte recognition material in the desired pattern.

Figure 3:
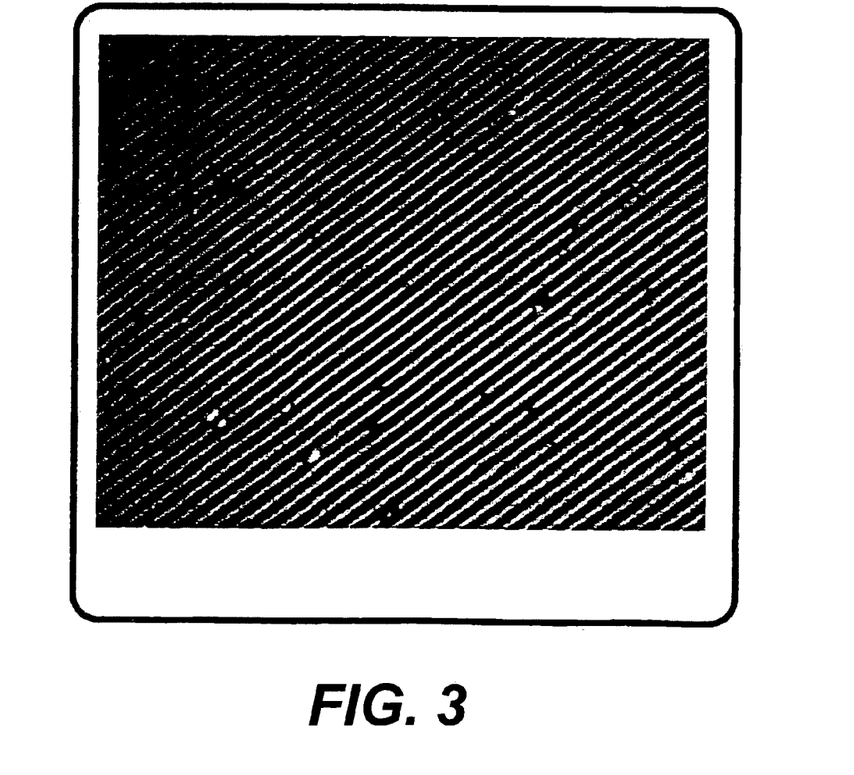
FIG. 3 is a micrograph of an analyte recognition material deposited on a grating surface suitable for use in a grating sensor according to the present invention.

FIG. 3 shows IgG proteins patterned onto glass microscope slides using microcontact printing. A PDMS stamp is used to deposit Alexa 488 labeled rabbit anti-goat IgG on a glass microscope slide. The fluorescent label was used in order to record an image using the fluorescent microscope. The data from the 4 µm period lines was recorded using a 40× magnification.

Photolithographic techniques are also well known as a method to manufacture a photoresist material in a desired pattern. In this technique, a patterned photoresist masks regions of the substrate that are to be functionalized with an analyte recognition material and allow the placement of surface pacifying molecules. Once the photoresist is removed there will be rows of molecular functional groups, primed for further chemical attachment to an analyte recognition material, such as an antibody, patterned between rows of nonreactive, protein resistant surface bound species. A photolithographic process can potentially move the surface chemistry methodology is advantageous in larger scale manufacturability and greater reproducibility.

A further patterning method includes a photochemical method. For example, a silane monolayer may be chemisorbed onto the surface of an etched grating wafer. The silane is chosen to have a reactive functional group (e.g., thiol, amine) available for further reaction. Specific bifunctional linkers are chosen that contain a photoactive functional group at one end. These linkers will be covalently attached to the silane film such that the photoactive group is available for further reaction/modification. The substrates may then be positioned into the optical assembly, and light from a UV laser source used to create an interference pattern on the substrate that matches the etched grating groove period. This will produce surface patterned lines of active and nonactive functional groups. The active silane functional groups are then linked to an analyte recognition material, such as an IgG antibody. The linker molecules used in such a method is chosen depending on the analyte recognition material to be attached and the light to be used in patterning. A variety of photoactive bifunctional linkers is commercially available of which many are reactive towards UV light of ~230–350 nm.

Further exemplary methods of analyte recognition material deposition and binding to a grating surface are detailed in references 3–5 and 8–11.

Following deposition of a surface chemistry component, such as a linker or an analyte recognition material, various techniques, such as ellipsometry, and atomic force microscopy (AFM) may be used to evaluate the deposition for artifacts and/or appropriate quantity and pattern.

Although the individual grating is discussed above as incorporating a single type of analyte recognition material, it will be recognized that a grating may incorporate more than one type of analyte recognition material in order to allow multiple analyte detection on single grating surface. In another embodiment, a grating structure can be configured to detect multiple analytes by overlaying multiple gratings in a single grating structure, much like a volume hologram, with each grating tailored to a specific analyte. In this case, differentiating between grating signals is achieved by utilizing different grating periods or by using several wavelengths.

Non-Specific Binding

Prevention of nonspecific binding of analytes and/or analyte recognition materials to a grating used in an inventive sensor is important in achieving an optimal signal to noise ratio. A number of different approaches have been used to reduce nonspecific binding to various surfaces. The adsorption of innocuous proteins such as bovine serum albumin (BSA) and casein has been used to block other proteins from binding during surface immobilization of antibodies. The attachment of poly (ethylene glycol) (PEG) groups to glass and metals has been an effective method of creating protein-resistant surfaces. Detergents, in particular non-ionic types such as the Tween and Triton series of surfactants and zwitterionic surfactants, have been used create "wetter" surfaces that inhibit protein surface adsorption.

Relative Position of Individual Gratings

The grating structure included in the grating sensor includes two individual gratings as described above. The individual gratings are variably configured with respect to each other dependant on factors such as grating geometry, diffraction order selection, wavelength of the light source used and the distance between the gratings.

As mentioned above, the two gratings, each having a periodic structure, are positioned parallel to each other, such that the periodic slits are superimposed and shifted laterally relative to each other. This lateral shift is less than one period and is preferably a shift of one quarter period. This arrangement is shown in FIG. 1, where the individual gratings are labeled 15 and 16, as well as in FIG. 6B where the individual gratings are labeled 110 and 120.

Figure 6A:
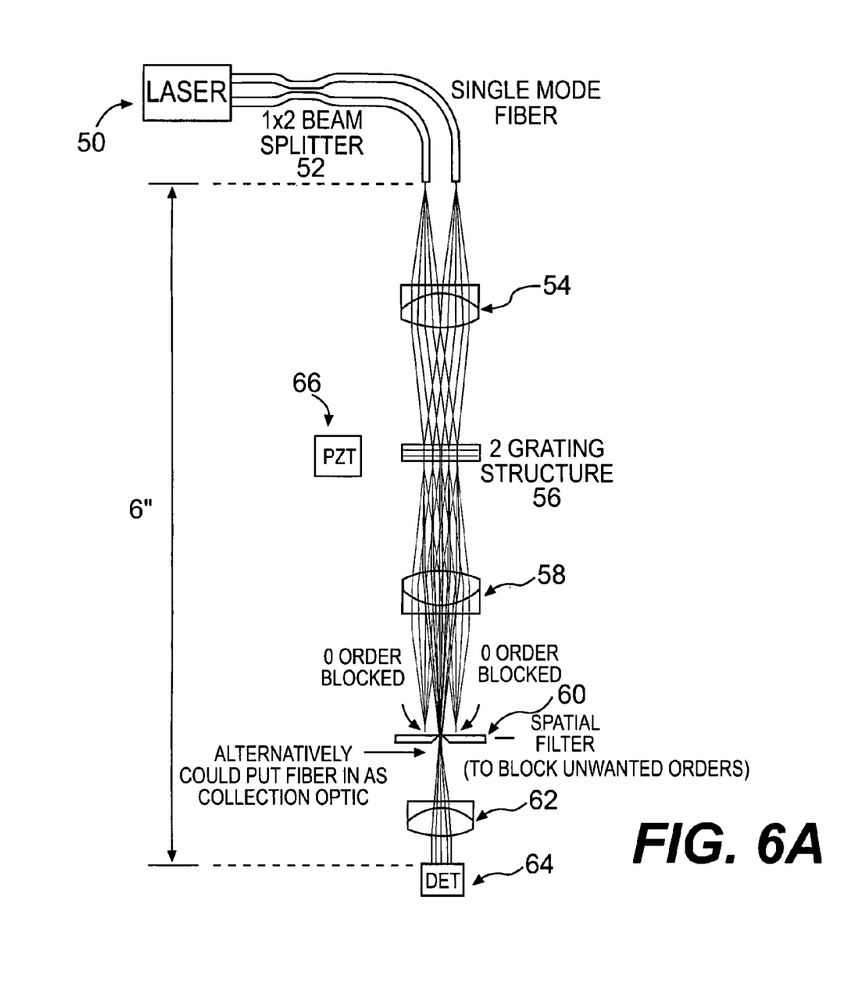
FIG. 6A is a drawing illustrating an embodiment of a grating sensor according to the present invention.
Figure 6B:
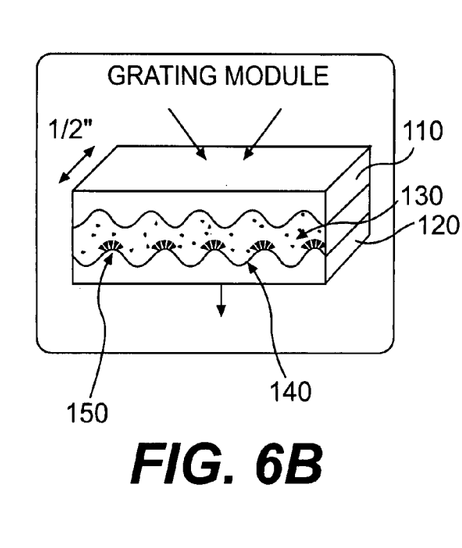
FIG. 6B is a drawing illustrating a grating sensor module according to the present invention.

In one embodiment, as shown in FIG. 6B, a first grating 120, having a surface 140 containing an immobilized analyte recognition material 150, is disposed proximate to a second grating 110 such that a space 130 is formed between the two gratings. Materials illustratively including a buffer or a sample putatively containing an analyte to be detected may be introduced into the space 130.

In an alternative embodiment, shown in FIG. 1, a first grating 16, having a surface 21 containing an immobilized analyte recognition material 18, and an opposing surface 22, is disposed proximate to a second grating 15 such that the surface 21 is distal to the grating 15 and the opposite surface 22 is proximal to the grating 15. This embodiment further includes a support 23 on which grating 16 is disposed, creating a space 19 between the grating 16 and support 23. Materials illustratively including a buffer or a sample putatively containing an analyte to be detected may be introduced into the space 19.

In the transverse dimension, the gratings are disposed with a minimum distance between them that allows fluid flow, typically greater than 1 nm. The maximal distance between gratings is defined by the width of the incident beam, the period of the grating, the wavelength, and the order of diffraction detected. In general, if the two gratings lie within the Rayleigh range or depth of focus of the incident beam, the minimum distance requirement is satisfied.

Multiple Agent Detection

Figure 7A:
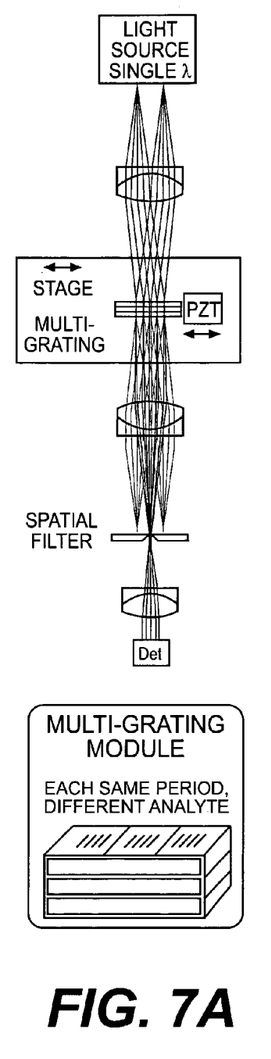
FIG. 7A is a drawing illustrating an embodiment of a grating sensor according to the present invention.
Figure 7B:
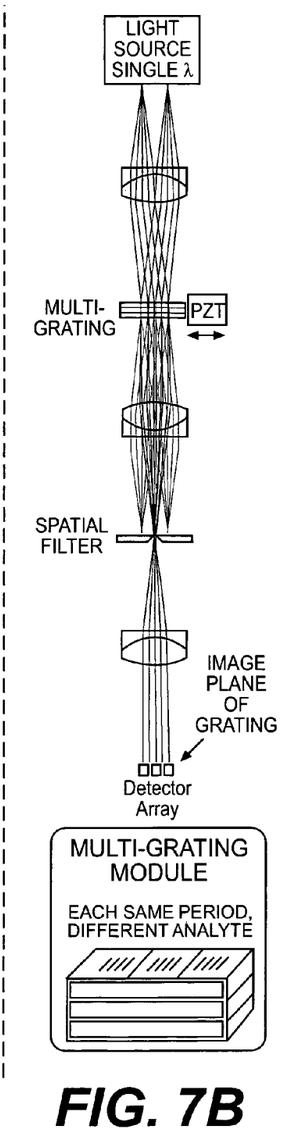
FIG. 7B is a drawing illustrating an embodiment of a grating sensor according to the present invention.
Figure 7C:
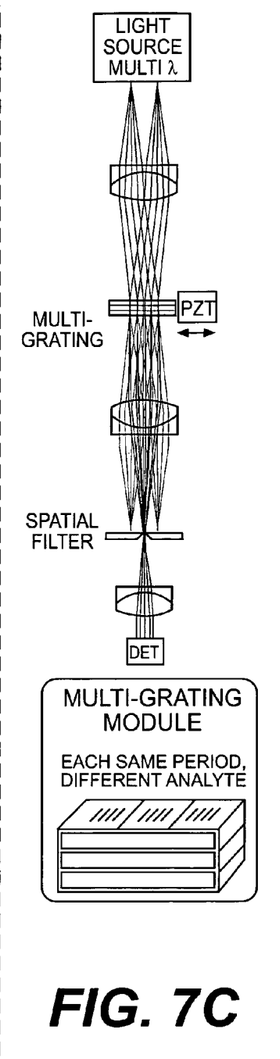
FIG. 7C is a drawing illustrating an embodiment of a grating sensor according to the present invention.

More than one analyte may be detected using multiple analyte recognition materials and multiple gratings as illustrated in FIGS. 7A, 7B and 7C as described in Examples 3, 4, and 5.

Illumination

Any wavelength of light which is not significantly absorbed by either the grating or the solution may be used for illumination in a sensor of the invention. Typically, a single wavelength is used, for example, 633 nm emitted by a He—Ne laser. In some multiple analyte detection systems according to the present invention, multiple wavelengths are used, each detecting a separate analyte as described below and as shown in FIG. 7C.

The grating structure is illuminated by two collimated beams, each at a specific angle, to achieve the interference between the desired first orders. The diffraction angle for a given period is wavelength dependent (see grating equation). Beam diameter is somewhat flexible. At the low end, the beam should at least cover at least two periods, but the diameter is small and the Raleigh range is short. At the high end, a large-diameter beam requires real estate and sufficient coverage in conjunction with the fabrication technique. Accordingly, the optimum is somewhere between the low and high ends.

Detector

A detector to be used in a sensor according to the invention is known in the art and includes such devices as oscilloscopes, digital cameras, CCD cameras and the like. The detection scheme is, for example, a derivative of a lithographic overlay alignment method, currently used in lithographic projection systems, which can detect lateral shifts of semiconductor wafer features down to the 10 nm range. Such detectors are described in, for example, U.S. Pat. Nos. 5,559,601 and 5,477,057.

A detector array may be used, for example, when multiple analytes are detected as shown in FIG. 7B.

Phase measurement is a very mature technology, such as is known in the field of commercial interferometry, and has inherent advantages over intensity measurements with regard to noise sources. Methods and devices for phase measurement are well known and commercially available.

Positioning System

A grating sensor according to the invention optionally includes a positioning system to dither the translation motion of the grating structure so as to modulate the baseline signal. Such positioning systems are known in the art and include piezo actuators such as piezoelectric transducers (pzt) commercially available and art recognized equivalents.

In another embodiment, a translation device with no moving parts is used, employing acoustically induced optical grating, for example.

Grating Sensor Theory of Detection

Information on grating sensor operation is as follows: given two electromagnetic waves of the form:

$$E_1(x,y,z,t) = A_1(x,y,z) e^{i(wt - \phi_1(x,y,z))} \quad (1A)$$

&

$$E_2(x,y,z,t) = A_2(x,y,z) e^{i(wt - \phi_2(x,y,z))} \quad (1B)$$

where: A is the amplitude and φ is phase of the wave.

The two beam interference equation for two beams of the same polarization and optical frequency is:

$$I(x,y,z) = I_1 + I_2 + 2 \sqrt{I_1 I_2} \cos(\Delta\phi(x,y,z)) \quad (2)$$

where: I is the intensity of the field and is equal to the modulus squared of the electric field, Δφ is the phase difference (φ₁−φ₂) between the waves.

From (2), it can be seen that the detected intensity varies cosinusoidally with the phase difference between the two waves. The alternating bright and dark bands are referred to as interference fringes.

In the grating sensor device a sinusoidal phase grating is used and can be defined by the transmission function:

$$t(x,y) = e^{i \frac{m}{2} \sin(2\pi f x - \psi)} \mathrm{rect}\left(\frac{x}{l}\right) \mathrm{rect}\left(\frac{y}{l}\right) \quad (3)$$

where: m is the peak to peak excursion of phase delay (depth modulation), f is the grating frequency, ψ, is the lateral 'shift' of the grating, rect is rectangular shaped aperture function with width l.

The far-field diffraction pattern when the transmission function of equation (3) is illuminated by a normally incident monochromatic plane wave is given by:

$$E(x_{\mathit{ff}}, y_{\mathit{ff}}) = K \sum_{q=\infty}^{\infty} \left( J_q\left(\frac{m}{2}\right) \mathrm{sinc}\left(\frac{1}{\lambda z}(x_{\mathit{ff}} - qf\lambda z) e^{iq\psi}\right) \right) \quad (4)$$

where: $x_{\mathit{ff}}$, $y_{\mathit{ff}}$ are the far-field transverse coordinates, q is the order of diffraction, K is a constant with all the terms not dependent on q lumped in, $J_q$ is a Bessel function of the first kind, order q, λ is the wavelength.

From (4), it can be seen that the introduction of the phase grating has deflected energy out of the zero order into a multitude of higher order components. The intensity of these orders is dependent on Jq(m/2) and phase of the orders is dependent on ψ, i.e. the shift, of the gratings as given by $e^{iq\psi}$.

Where the system is set up such that the +1 and −1 orders are made to coincide so as to generate a two beam interference condition as in equation (2), one beam would have an electric field of $E_{+1} \propto e^{i\psi}$ while the second would have $E_{-1} \propto e^{-i\psi}$. Equation (2) becomes:

$$I = I_{+1} + I_{-1} + 2 \sqrt{I_{+1} I_{-1}} \cos(2\psi) \quad (5)$$

Thus the interference pattern now becomes dependent on the 'shift' of the grating. Measurement of the fringes can yield the lateral position of the grating. This is the basis for some of the techniques used to align wafer in lithography as described, for example, in U.S. Pat. Nos. 5,559,601 and 5,477,057.

Measurement of phase to yield the lateral shift of a grating can be very precise and relates to changes in the depth of modulation. Depth of modulation can be converted to a lateral shift in position of a grating by placing two gratings adjacent to each other with one shifted by a ¼ grating period. Using some trigonometric relationships, it can be shown that:

$$A_1 \sin(x) + A_2 \cos(x) = A_3 \sin(x+\psi) \quad (6)$$

where: A is the amplitude of the sinusoidal components and ψ is the shift of the composite grating.

ψ is given by:

$$\psi = \arctan\left(\frac{A_2}{A_1}\right) \quad (7)$$

Figure 4:
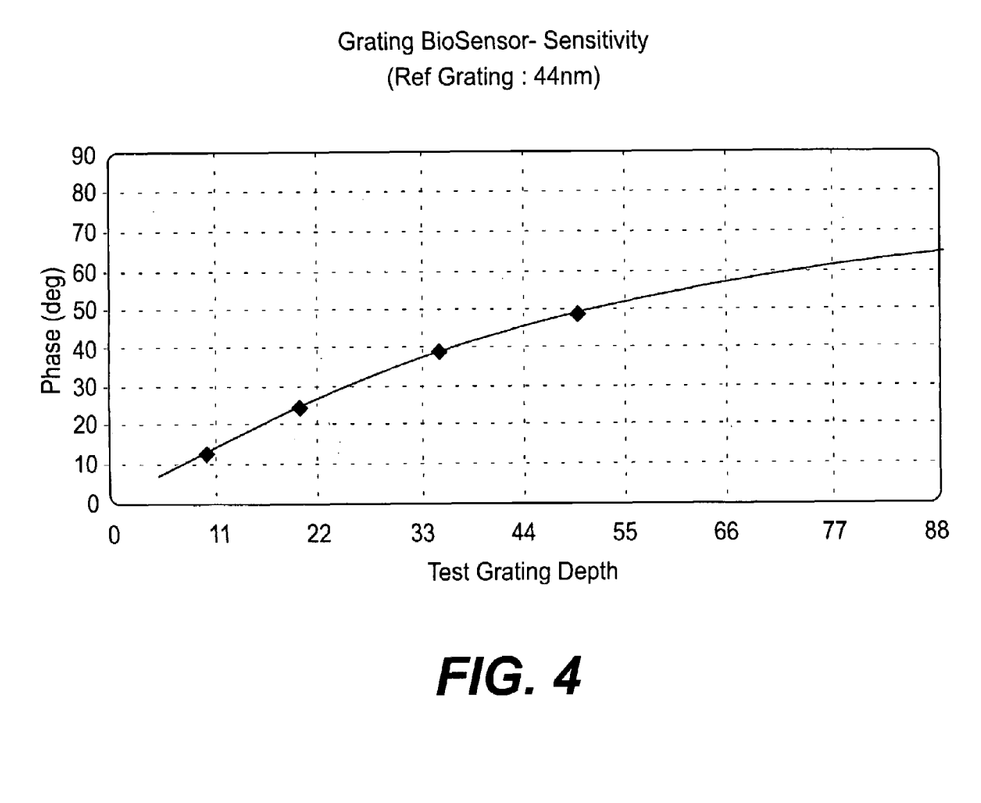
FIG. 4 is a graph of grating shift plotted vs. the ratio of the depths of the two gratings.

Therefore the shift of this grating structure is dependent on the relative amplitudes of the two individual gratings which make it up. If $A_1$ is much larger than $A_2$, then ψ approaches zero and equation (5) is at a maximum. If $A_1$ is much smaller than $A_2$, then, ψ approaches 90 degrees and equation (5) is at a minimum. Moving between these two conditions would result in the detected intensity pattern to shift from a maximum to a minimum, i.e. the interference pattern would shift ½ fringe. FIG. 4 is a graph of equation 7 with ψ or grating shift plotted vs. the ratio of the depths of the two gratings. In FIG. 4, one grating with a 44 nm depth is held constant and is called the reference grating. The other gratings depth is caused to vary so as to trace out the curve. Therefore, at 44 nm the ratio=1 for the grating depths. Note that the shift of the grating is given in degrees not length which may be confusing. The shift is relative to the grating period. A shift of 360 degrees would be a shift of 1 period. A 90 degree shift is ¼ of a period. Measurement of the optical phase change between two interfering orders indicates a change in the ratio of the two grating amplitudes.

Commercial interferometry systems are available whose minimum detectable limits are in the 1/1000 of a phase cycle. From FIG. 4 it can be seen that this technique has potential sensitivity to detect fractions of a 1 nm in grating height change.

Grating Sensor in Operation

Steps of a method according to the invention for using the inventive grating sensor include a preliminary illumination of the grating structure before exposure to the sample or analyte in order to establish a baseline optical phase signal.

In an optional step of the inventive method, the grating structure is treated to inhibit non-specific binding of analyte to analyte recognition material. Typically, the grating is exposed to a surfactant, such as a dilute solution of TWEEN-20. Alternatively, a protein known not to specifically bind to the analyte recognition material is use, such as bovine serum albumin or the like. Following treatment for non-specific binding, the grating may be rinsed to remove any excess.

In a further step of the inventive method, a grating having an analyte recognition material is exposed to a sample putatively containing an analyte known to bind to the analyte recognition material disposed on the grating. The sample is exposed to the grating under conditions that will allow binding of the analyte to the analyte recognition material. Binding conditions for specific analyte/analyte recognition materials are known in the art. Variables such as temperature, salt concentrations, pH and reaction time are known to affect binding and one of skill in the art will recognize the appropriate binding conditions for a particular analyte/analyte recognition material pair. Specific conditions are set forth in common references such as, for example, Bowtell et al., DNA Microarrays: A Molecular Cloning Manual, Cold Spring Harbor Laboratory; 2002; Sambrook et al., Molecular Cloning: A Laboratory Manual, Cold Spring Harbor Laboratory; 3rd edition, 2001; and Harlow et al., Using Antibodies: A Laboratory Manual: Portable Protocol NO. I, Cold Spring Harbor Laboratory; 1998.

A sample may be a biological or chemical sample, such as a sample obtained from a human or other animal or from an environmental site where the earth, water or air are to be tested. A sample illustratively refers to a cells, tissue or physiological fluid, such as amniotic fluid, blood, cerebrospinal fluid, plasma, serum, saliva, semen, and other bodily fluids. A sample also includes fluid or a suspension of solids obtained from mucous membranes, wounds, tumors and organs. Further, a sample may be obtained to test for environmental contamination. For example, a surface, such as an air filter, suspected to be contaminated may be swabbed and the material obtained may be suspended in a solution for exposure to a grating.

Advantageously, neither the analyte nor the analyte recognition material is required to be labeled in a method according to the present invention. This allows faster processing of samples, while affording highly sensitive detection of analyte.

The exposure of the grating to the sample may be achieved in situ, that is, with the grating in place in the grating structure. For example, the sample may be introduced into the space between the two gratings. FIG. 6B shows such a space 130. The sample may be introduced through an inlet port 11 such as is shown in FIG. 1 and removed via the same port following binding. Alternatively, the sample may be removed through an outlet port 13, such as is shown in FIG. 1.

Exposure of the grating to the sample may also be accomplished with the grating removed from the grating structure. For example, the sample may be applied to the grating, or the grating may be immersed in the sample, for the time required by the binding reaction. Subsequently, the grating may be placed in the grating structure.

Optionally, the grating is rinsed following exposure to the sample in order to remove excess sample and to stop the binding reaction.

Following exposure of the grating to the analyte, the grating structure is illuminated and the optical phase signal detected. Any change in the optical phase signal may be quantitated by comparison to the optical phase signal detected during the preliminary illumination step.

Optionally, the amount of analyte present in the sample is calculated as described above.

EXAMPLES

Example 1

Figure 5A:
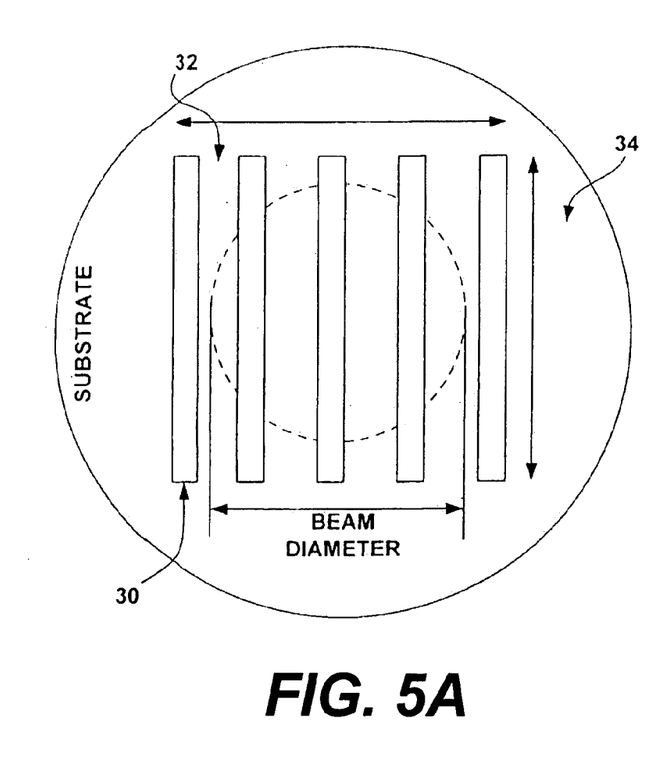
FIG. 5A is a drawing illustrating a top view of a grating suitable for use in a grating sensor according to the present invention.
Figure 5B:
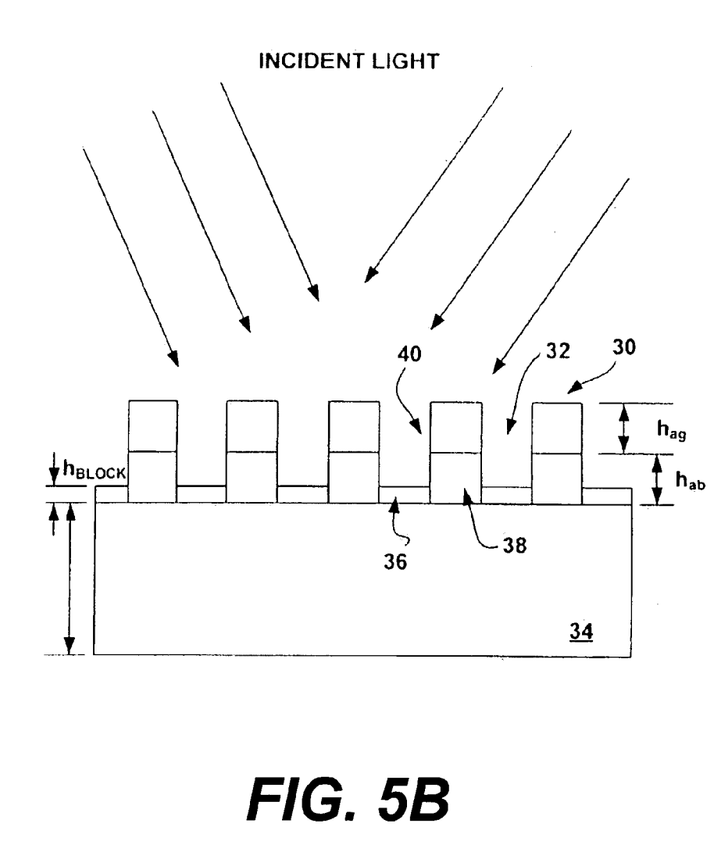
FIG. 5B is a drawing illustrating a side view of a grating suitable for use in a grating sensor according to the present invention.

FIGS. 5A and 5B illustrate a detailed view of a grating. Molecular receptors, such as antibodies, are placed in precise locations on an optical substrate. In this case, the antibody receptors lie in 2 μm wide lines 30 with 2 μm wide separations 32 (a 4 um period) and are placed on a substrate 34 made of fused silica. This 4 um period will produce $1^{st}$ order diffraction angle of ~9 degrees at a wavelength of 633 nm. Blocking material 36 to prevent non-specific binding of receptors and analyte may be placed in the region between the lines. Upon introduction of buffer solution putatively containing the antigen corresponding to the chosen antibody, specific binding between immobilized antibody 38 and analyte 40 occurs at precise locations, i.e. at the peaks of the grating. This molecular binding changes the physical and optical height [(index)×(change in height)] of the grating. In this example, the heights of the antibody ($h_{ab}$)+antigen ($h_{ag}$) layers are expected to be in the 10's of nm range. An average change in height over the illuminated region from 10 nm to 20 nm upon binding generates a sufficient signal for adequate detection. It is also expected that the incident beam would have to cover at least 2 cycles or periods in order to generate a sufficient signal.

Example 2

FIG. 6A shows an optical schematic of a system for detecting a single analyte. In the figure, the light source is a laser 50 emitting coherent light at a wavelength of 633 nm. This light is introduced into a beamsplitter 52 such that two point sources are created. A commercially available single mode fiber optic coupler can be used. These two point sources are then collimated by a lens 54 and directed towards the grating structure. The collimated beams are incident upon the grating structure 56 at an angle corresponding to the +1 and −1 diffraction orders generated by a 4 um period grating. This yields a ~9 degrees angle of incidence. By using a lens with a 25 mm focal length a point source separation of 7.8 mm at the output of the fiber coupler can be realized. Two gratings, such as that depicted in FIG. 5 are used in the grating structure 56. The two gratings are translated by ¼ period with respect to each other and the separation between the two allows for fluid flow. A grating structure shown has a transverse dimension of ½ inch as shown is adequate for optical coverage while allowing for fluid flow through the grating structure. The light passing through the grating from each incident beam is diffracted. In this configuration the +1 order of one beam is coincident and therefore interferes with the −1 diffraction order of the other beam. Both beams in turn are coincident with the optical axis of the system. The grating is followed by another lens 58 which focuses the diffracted light into the far-field plane. A spatial filter 60 placed at the far-field plane eliminates the light from the unwanted orders and allows the interfering overlapped orders to pass. A collection lens 62 directs the light onto a single detector 64. Because of the interference, the intensity of the light at the detector is indicative of the phase difference between the two diffracted beams. This phase difference in turn is indicative of the lateral translation of the grating structure which in turn is indicative of the relative heights of the two gratings which make up the grating structure as previously explained. Modulation of the detected signal can be provided by mounting a piezoelectric transducer (pzt) 66 to the grating structure. The pzt provides precise lateral movement of the grating and therefore a precise mechanism for introducing a known phase difference in the interfering beams. Changes in the phase caused by the binding event will show up as an electrical phase shift in the modulated signal. It is important to note that the optical schematic of FIG. 6A is a real ray-trace (carried out using lens design software, OSLO) using off the shelf lenses (Edmund Scientific) which demonstrates that with relatively moderate effort the system can be made compact. In FIG. 6A, the distance from the output of the fibers to the detector is approximately 6 inches.

Example 3

Multiple Analyte Detection—FIG. 7

Several detection configurations for multiple analyte detection are depicted in FIG. 7.

The layout shown in FIG. 7 can be adapted to accommodate multiple analyte detection by modifying the grating assembly to include multiple gratings, each designed to detect different analyte. The grating structure may be placed on a stage such that each grating may be translated to pass under the probing beam of the optical system, much like a 'stepper' in photolithography. FIG. 7A illustrates such a system. Such gratings range in size from 10 um and greater.

Example 4

FIG. 7B shows the grating structure imaged onto a multi-material detector array, a CCD camera for example. The grating structure is broadly illuminated. i.e. all gratings are simultaneously illuminated. Each detector 'sees' only a portion of the grating structure. Judicious location of the spatial filter plane assures that the light that enters the detectors is limited to the desired interfering diffracted orders as previously described.

Example 5

FIG. 7C shows a grating sensor including a multi-wavelength light source. The grating assembly containing multiple gratings is broadly illuminated by the light from this source at a specific angle for all wavelengths. Because the diffraction angle for a given period is wavelength dependent (see grating equation), the period of the individual gratings is different from grating to grating. In this way, only light of a specific wavelength for each grating will be diffracted into to proper angle to pass the spatial filter and into the detector. At the detector, each wavelength represents the signal from one of the gratings. At this point, a spectral filter may be used to switch between the wavelengths and therefore the different gratings. Alternatively, because each grating may have a different period, each grating may generate a different signal frequency as the PZT translates the grating. Therefore at the detector, the frequency of the signal is indicative of a specific grating and therefore a specific targeted analyte while the phase of the frequency component indicates a binding event.

Example 6

Figure 8:
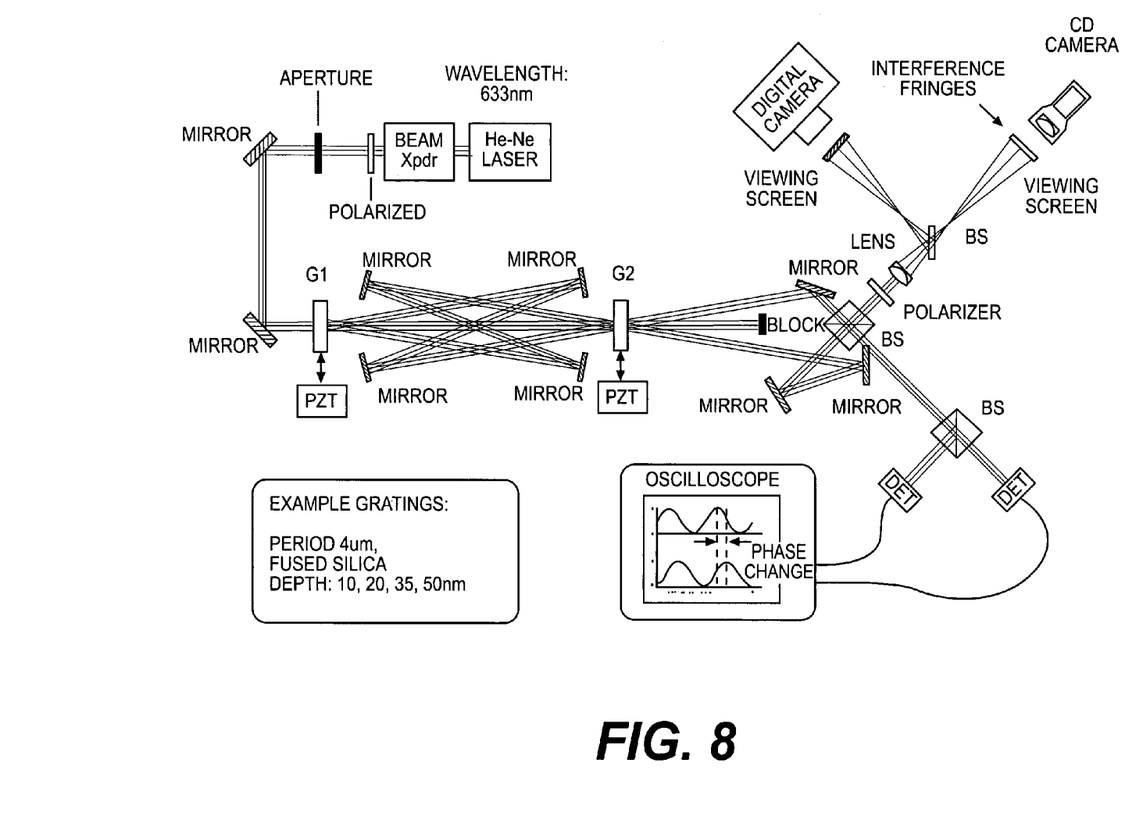
FIG. 8 is a drawing illustrating an embodiment of a grating sensor according to the present invention.

FIG. 8 illustrates another embodiment of the grating sensor. Light from a frequency stabilized He—Ne is incident upon two separate gratings. Illumination will only be at the zero order (or normal incidence) angle. The two gratings are separated in order to gain some flexibility in alignment and in removing and inserting test gratings. The layout with the two gratings is optically equivalent to the two gratings superimposed. The diffracted light into the +1 an −1 orders for both gratings are overlapped and made to interfere at the exit of the cube beamsplitter. This configuration is reversed from that of FIG. 6A. That is, in FIG. 6A the light is incident upon the gratings in two beams at the +1 and −1 diffraction orders. A single beam at the zero order diffraction angle is detected. In FIG. 8, the light is incident upon the gratings in the zero order and the diffracted +1, −1 orders are detected. The two configurations are optically equivalent (light is reversible) while the configuration shown in FIG. 8 confers ease of alignment. FIG. 8 illustrates three ways to view the data. A CCD and/or a digital camera records the two dimensional interference patterns while the individual detectors look at single point in the interference pattern. The $2^{nd}$ single detector can be used as a reference. A single detector yields simple quantitative data with regard to the change in phase. The data from the CCD camera may also be analyzed to yield quantitative data or used to get a quick visual of the changes in the interference pattern.

Example 8

FIG. 9 shows results of use of optical glass gratings without an analyte recognition material. A series of such gratings, each with a different grating modulation depth, is created in the etching process used to make fused silica gratings. The gratings are produced to have precise modulation depths such as 10 nm, 20 nm, 35 nm, and 50 nm. Tests are performed using two such gratings at a time to record the differences in these grating heights. These glass gratings may also serve as a reference or calibration to the set up to be compared against the signal generated by a grating containing an analyte recognition material.

Figure 9A:
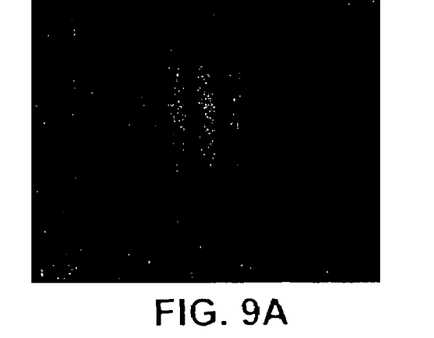
FIG. 9 is a digital image of an interferogram.
Figure 9B:
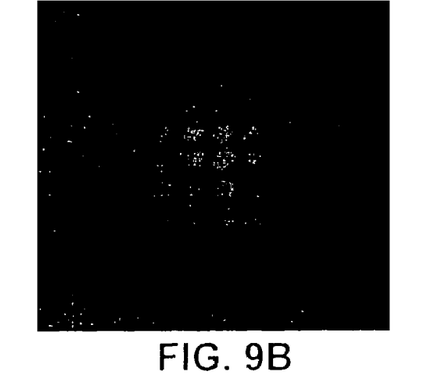
Figure 9C:
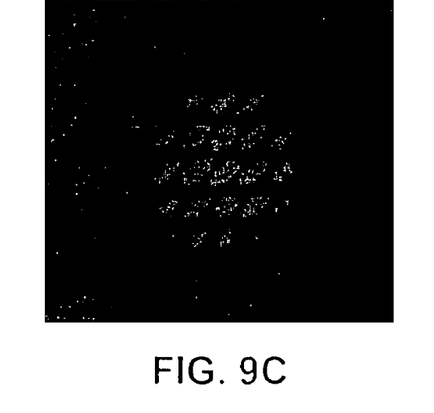

Interferograms recorded using a digital camera, a wavelength of 633 nm and optical glass gratings without an analyte recognition material are shown in FIG. 9. Tilt fringes have been introduced so as to indicate the effect of varying the depth of one of the two gratings. Adding this tilt is equivalent to adding a variable translation across the grating as a function of position. In other words, the tilt fringes assures that at some places the two gratings are displaced relative to each other by the required ¼ period while at other places the gratings are exactly overlapped with no equivalent displacement. Because the shift in the optical phase as a function of grating depth is only apparent when the displacement is ¼ period, the deviation of the tilt fringes is a measure of the depth ratio difference between the two gratings. The reference grating used has approximately 50 nm of etch depth. FIGS. 9A, 9B, and 9C are the interferograms when the reference grating is paired with gratings of 0 nm, 20 nm and 50 nm of etch depth respectively. Note the degree of 'slant' changes with etch depth. This is an indication of the change in the maximum deviation of the tilt fringes and shows that at these small etch depth levels that there is a substantial change in the interferogram patterns.

REFERENCES (1) Gallatin, G. M, et al, "Mask and Wafer Diffraction Grating Alignment System wherein the Diffracted Light Beams Return Substantially along an Incident Angle", U.S. Pat. No. 5,559,601, 1996.

(2) Angeley, D. G., et al, "Off Axis Alignment System for Scanning Photolithography", U.S. Pat. No. 5,477,057, 1995.

(3) Sanford, M. S., et al, "Photoactivatable Cross-Linked Polyacrylamide for the Site-Selective Immobilization of Antigens and Antibodies", Chem Mater. 1998, 10, 1510–1520.

(4) Morhard, F., et al, "Immobilization of antibodies in micropatterns for cell detection by Optical Diffraction", Sensors and Actuators B 70 (2000) 232–242.

(5) St. John, P. M. et al, "Diffraction-Based Cell Detection Using a Microcontact Printed Antibody Grating", Anal Chem, Vol. 70, No. 6, Mar. 15, 1998.

(6) Everhart, D. S., et al, "Optical Diffraction Biosensor", U.S. Pat. No. 6,060,256, 2000.

(7) Goodman, J. W., "Introduction to Fourier Optics", McGraw-Hill, 1968.

(8) X Bhatia, S. K., et. al.; "Fabrication of Surfaces Resistant to Protein Adsorption and Applications to Two-Dimensional Protein Patterning", Anal. Biochem. 1993, 208, 197.

(9) Pritchard, D. J., et. al.; "Patterning and Regeneration of Surfaces with Antibodies", Anal. Chem. 1995, 67, 3605

(10) Brooks, S. A., et.al.; "Segregation of Micrometer-Dimension Biosensor Materials on a Variety of Substrate Surfaces", Anal. Chem. 2000, 72, 3253

(11) Liu, X.-h., et. al.; "Photopatterning of Antibodies on Biosensors", Bioconj. Chem. 2000, 11, 755.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. An optical sensor comprising:
   a first periodic diffraction grating;
   a second periodic diffraction grating, the gratings being superimposed and shifted laterally relative to each other by a distance of less than one period;
   an analyte recognition material disposed on a surface of the second diffraction grating;
   an illumination source directing illumination onto the first grating; and
   a detector disposed relative to the second grating such that illumination passing through the second grating reaches the detector.

2. The optical sensor of claim 1, further comprising a positioning system for moving the first and second gratings.

3. The optical sensor of claim 1, further comprising a spatial filter disposed relative to said second grating such that selected orders of diffracted light are prevented from reaching the detector.

4. The optical sensor of claim 1, wherein the distance of less than one period is ¼ period.

5. The optical sensor of claim 1, wherein the analyte recognition material is an antibody.

6. The optical sensor of claim 1, wherein the analyte recognition material is a nucleic acid.

7. The optical sensor of claim 1, wherein the analyte recognition material is a lectin.

8. A method of detecting an analyte, comprising the steps of:
   providing the optical sensor of claim 1 with the illumination source activated;
   sampling the output of the detector to establish a baseline optical phase signal;
   exposing the analyte recognition material to the sample;
   sampling the output of the detector to determine a second optical phase signal; and comparing the baseline optical phase signal to the second optical phase signal to detect the presence of the analyte, if any in the sample.

9. The method of claim 8, wherein the sample is obtained from a mammal.

10. The method of claim 9, wherein the mammal is a human.

11. The method of claim 8, wherein the sample is obtained from an environment.

12. The method of claim 8, wherein the optical sensor further comprises a positioning system for moving one or both of first and second gratings.

13. The method of claim 8, wherein the optical sensor further comprises a spatial filter disposed relative to the second grating such that selected orders of diffracted light are prevented from reaching the detector.

14. The method of claim 8, wherein the distance of less than one period is ¼ period.

15. The method of claim 8, wherein the analyte recognition material is an antibody.

16. The method of claim 8, wherein the analyte recognition material is a nucleic acid.

17. The method of claim 8, wherein the analyte recognition material is a lectin.

18. The method of claim 8, further comprising the step of comparing the first and second optical phase measurements to quantitate the analyte in the sample.

19. An optical sensor configured for use with an illumination source and a signal detector, comprising:
   a first periodic diffraction grating;
   a second periodic diffraction grating, the gratings being superimposed and shifted laterally relative to each other by a distance of less than one period such that the illumination from the source is affected by both gratings before reaching the detector; and
   an analyte recognition material disposed on the surface of the second diffraction grating.

20. The optical sensor of claim 19, further comprising a positioning system for moving one or both of the first and second gratings.

21. The optical sensor of claim 19, further comprising a spatial filter disposed relative to the second grating such that selected orders of diffracted light are presented from reaching the detector.

22. The optical sensor of claim 19, wherein the distance of less than one period is ¼ period.

23. The optical sensor of claim 19, wherein the analyte recognition material is an antibody.

24. The optical sensor of claim 19, wherein the analyte recognition material is a nucleic acid.

25. The method of claim 19, wherein the analyte recognition material is a lectin.

* * * * *